United States Patent
Huang et al.

(10) Patent No.: US 8,633,711 B2
(45) Date of Patent: Jan. 21, 2014

(54) INDUCTIVE COAGULATION SENSORS AND DEVICES

(75) Inventors: Michael Huang, Santa Clara, CA (US); Mengya Wu, Santa Clara, CA (US); Mengyou Wu, Santa Clara, CA (US)

(73) Assignee: MicroPoint Bioscience, Inc., Santa Clara, CA (US)

(*) Notice: Subject to any disclaimer, the term of this patent is extended or adjusted under 35 U.S.C. 154(b) by 690 days.

(21) Appl. No.: 12/807,698

(22) Filed: Sep. 9, 2010

(65) Prior Publication Data

US 2011/0109325 A1    May 12, 2011

Related U.S. Application Data

(60) Provisional application No. 61/278,665, filed on Oct. 9, 2009.

(51) Int. Cl.
*G01R 27/28* (2006.01)
*G01R 27/26* (2006.01)

(52) U.S. Cl.
CPC .................. *G01R 27/2611* (2013.01)
USPC ........................................ 324/656

(58) Field of Classification Search
None
See application file for complete search history.

(56) References Cited

U.S. PATENT DOCUMENTS

| | | | |
|---|---|---|---|
| 5,892,144 A | 4/1999 | Meller et al. | |
| 6,200,532 B1 | 3/2001 | Wu et al. | |
| 6,673,622 B1 | 1/2004 | Jina | |
| 7,144,495 B2 | 12/2006 | Teodorczyk et al. | |
| 7,598,094 B2 * | 10/2009 | Masters et al. | 436/526 |
| 2005/0155415 A1 | 7/2005 | Kurowski et al. | |
| 2008/0160500 A1 | 7/2008 | Fuller et al. | |
| 2008/0224688 A1 | 9/2008 | Rubinsky et al. | |
| 2009/0246078 A1 | 10/2009 | Barnard et al. | |

OTHER PUBLICATIONS

International Search Report and Written Opinion for PCT/US2010/002470, (May 2011).

* cited by examiner

*Primary Examiner* — Paresh Patel
(74) *Attorney, Agent, or Firm* — Gary Baker; Quine Intellectual Property Law Group, P.C.

(57) ABSTRACT

This invention provides methods and devices for detecting the viscosity and conductivity of a conductive fluid sample. A sample fluid can be received into a sample chamber between a field inductor and sensor inductor. Electromagnetic fields generated by the field inductor can be modulated due to the counter-emf induced in the sample. The modulations can be detected by the sensor inductor and correlated to electric parameters in the fluid.

30 Claims, 5 Drawing Sheets

INDUCTIVE COAGULATION SENSORS AND DEVICES

CROSS-REFERENCE TO RELATED APPLICATIONS

This application claims priority to and benefit of a prior U.S. Provisional Application No. 61/278,665, Inductive Coagulation Sensors and Devices, by Michael Huang, et al., filed Oct. 9, 2009. The full disclosure of the prior application is incorporated herein by reference.

FIELD OF THE INVENTION

The invention is directed to devices and methods for detecting physical and electrical parameters of a conductive fluid. Exemplary devices include a sample chamber between a field inductor and a sensor inductor. The field inductor can be energized by an oscillator, and electromagnetic signals received by the sensor inductor can be detected by a voltage or current detector. Viscosity of a conductive fluid is measured by exposing the fluid to an electromagnetic field from a field inductor and monitoring currents, voltages or waveforms induced in the fluid. The fluid can be monitored by a sensor inductor in association with a detector. Viscosity or changes in viscosity of the fluid can be detected as modulations to the electromagnetic field resulting from counter-currents induced in the fluid.

BACKGROUND OF THE INVENTION

Various techniques have been used over the years to determine the coagulation status of blood. The standard in medical technology for some time was the fibrometer. Recently devices have been introduced that detect changes in the coagulation status of blood or plasma indirectly by measuring changes in electrical characteristics of the fluid with time.

A fibrometer is a device with a heat block to condition the temperature of a sample to be tested, a timer, and a mechanical probe that moves in the sample to detect when a clot has formed. A couple of drops of citrate anti-coagulated plasma is held in the heat block with the probe positioned above. At the instant a technician injects a coagulant into the plasma he presses a button that starts a timer and drops the moving probe down into the plasma. The timer stops at the time when the plasma becomes coagulated enough to stop the probe from moving. Of course, one can see that precision of this assay can vary significantly depending on the skill of the technician. In addition the sample size can be excessive, especially considering the confirmatory retesting typically required.

In U.S. Pat. No. 7,144,495, to Teodorczyk, the viscosity of a fluid is detected as changes in DC current flowing through the fluid with time. For example, an electric potential is applied to an electrochemical cell containing the fluid to first achieve a steady state cell current. A decrease in the steady state cell current is then detected and related to a change in viscosity of the sample. However, the method can be problematic because the fluid contact electrodes can be expensive in materials and construction. Further, use of DC current can exhaust current carriers in the sample, produce excessive heat, and generate gasses by electrolysis. These problems can affect the precision and consistency of the assay.

In U.S. Pat. No. 6,673,622, to Jina, an AC current is applied to a sample through contact with electrodes in a sample chamber. The viscosity of the sample is evaluated according to the impedance of the sample. Although this avoids some problems associated with DC current in Teodorczyk, the devices of Jina still require expensive electrode conductors, electrode contact with the sample, and careful sample handling for reproducible results.

In view of the above, a need exists for methods of coagulation analysis that do not require electrode contact with the sample. It would be desirable to measure sample viscosity over time without the assay itself influencing the sample. Benefits could also be realized through methods and devices that are less sensitive to variances in sample loading. The present invention provides these and other features that will be apparent upon review of the following.

SUMMARY OF THE INVENTION

The methods and devices of the invention include, e.g., a field inductor positioned adjacent to a sample chamber to expose a sample to an electromagnetic field. A sensor is provided to detect influences of field on certain measurable characteristics of the sample. The effects of the field on the sample can be correlated to physical and electrical properties of the sample.

The devices for sample analysis can include, e.g., a sample chamber inductively coupled with a field inductor. Changes in sample electrical properties resulting from exposure to the electromagnetic field of the inductor can be detected by a sensor. In a typical embodiment, the sensor is an inductor and the sample is a blood plasma. Currents are induced in the plasma by the field inductor, and the sample counter-emf causes perturbations in the primary field of the field inductor that can be detected by a sensor inductor. A reagent can cause the plasma to clot. The field perturbations detected over two or more time points can be correlated to the coagulation status of the plasma, e.g., to determine a clinical clotting time for the plasma.

The devices include a viscosity sensor comprising a field inductor, a sensor inductor, and a sample chamber comprising an electrically conductive sample of changing viscosity. The sample chamber is inductively coupled to the field inductor and inductively coupled to the sensor inductor, e.g., so that changes in the conductivity of a sample in the sample chamber will result in field changes ultimately detected by the sensor inductor.

In a particular embodiment, a viscosity sensor is provided comprising a field inductive coil, a sensor inductive coil, and a sample chamber between the field and sensor inductive coils with a volume less than 0.3 mm$^3$ between the coils. A conductive sample in the sample chamber would be inductively coupled to each of the field and sensor inductive coils. That is, even though the claimed device does not necessarily have a sample in the sample chamber, the device is configured so that when a conductive sample is placed in the sample chamber, current in the field inductor will induce a counter-emf in the sample fluid; and current in the sample fluid will induce a counter-emf in the sensor inductor. In preferred embodiments, the device is a microfluidic device, e.g., with microscale channels.

In another aspect of the invention, a conductivity (or viscosity, voltage, impedance, waveform, phase shift, and/or the like) sensor is based on induction of current in a layered device. For example, a conductivity sensor can be fabricated as a layered microfluidic chip. The sensor can include a first inductor in a first layer of the chip, a sample chamber in a second layer of the chip between the first layer and a third layer, and a second inductor in the third layer of the chip, so that a conductive fluid in the sample chamber would be inductively coupled to the first inductor and to the second inductor.

In still other aspects, the inductive sensor can have field and sensor inductors coupled essentially only through the sample. For example, the sensor can include a conductivity sensor having a sample conduit with a central axis, a first inductive coil of conductive material coiled around the sample conduit at a first position, a second inductive coil of conductive material coiled around the sample conduit at a second position separated from the first position by a sample space distance along the axis, a sample chamber in the conduit in the region of the sample space separation, and an electric field shield between the inductors, wherein the shield does not directly block electric fields in the sample space between the inductors. In this way, a conductive fluid in the sample space will be inductively coupled to the first inductive coil and inductively coupled to the second coil. This configuration can enhance the relative influence of sample counter-emf fields on the sensor inductor over primary field inductor fields. For example, the shield reduces or eliminates the phenomenon of field inductor field lines reaching the sensor inductor without going through the sample or being modulated by fields induced in the sample. In preferred embodiments, the shield is positioned to block relatively less inductive interaction with the sample than it blocks between the inductors.

In certain devices, changing viscosity of a sample is measured with paired field and sensor inductors. For example, a device to measure viscosity changes of a sample can include a sample port fluidly coupled to a sample chamber, a first (field) inductor inductively coupled to the sample chamber, a second (sensor) inductor inductively coupled to the sample chamber, an electronic detector in electrical contact with the second inductor, and a sample in the sample chamber with viscosity changing over time. With this arrangement, the sample viscosity changes with time are detectable by the detector as changes in signals from the second (sensor) inductor over time.

In certain embodiments, the sample chamber is positioned in a sample layer having opposite parallel planar surfaces, and the first and second inductors are positioned on opposite sides of the sample layer. In such embodiments, the first or second inductor can be, e.g., a conductive material coiled in a plane substantially parallel to a layer of a laminated cartridge. Alternately, the sample chamber is tubular with a central axis wherein the first and second inductors are coiled around the axis at opposite ends of the chamber. In preferred embodiments, the sample is stationary (not significantly moving or flowing) in the sample chamber during measurement of sample viscosity changes.

In many embodiments, the device further includes an electric field shield between the first and second inductors. Optionally, the inductors and/or sample chamber is shielded to reduce background noise from extraneous fields. Alternately, first (field) inductor is inductively coupled to the second (sensor) inductive coil.

The sample for analysis by the devices can include, e.g., any conductive fluid or gel. For example, the sample can be a biological fluid, blood, plasma clotted plasma, and the like.

The devices can include a reagent that reacts with a component of a sample of interest to provide a detectable product. For example, the chamber can include a reagent active in coagulating or polymerizing the conductive fluid.

The devices can include detectors, e.g., in electrical contact with the sensor inductor to determine a voltage, a current, a resistance, a waveform, a wavelength, a phase angle difference, and/or the like.

The present inventions include methods to determine an electrical parameter of a fluid. For example, the conductivity of a sample can be detected by inducing a current in the sample and measuring the parameter through sample contact electrodes. A conductivity sensor can comprise an inductor inductively coupled to a sample chamber comprising an inner surface, and further comprise an electronic detector in electrical contact with the inner surface through one or more detector electrodes. Thereby, an electrical current induced by the inductor on a sample in the sample chamber can be detected to determine an electrical conductivity of the sample, as detected through the electrodes. The conductivity of the sample can be correlated to the viscosity (which can influence the movement of carrier ions) of the sample to determine the viscosity of the sample.

Viscosity changes can be detected by measuring changes of current induced in the sample. A method of determining the viscosity of a conductive fluid can include, e.g., providing a sample chamber inductively coupled to a first (field) inductor and to a second (sensor) inductor, providing the conductive fluid in the sample chamber, providing an electronic detector in functional contact with the second inductor, generating an electric field in the first inductor, detecting with the detector an electric current or voltage induced in the second inductor by the electric field, and evaluating the detected current or voltage to determine the viscosity of the sample. In many embodiments, the detected electric current or voltage is induced in the sensor inductor by an electromagnetic field generated or modulated by current flowing in the conductive fluid. In certain embodiments, evaluating comprises determining a phase shift between the first (field) inductor output and a signal detected in the second (sensor) inductor, or determining a phase shift between the first inductor output and the current induced in the conductive fluid sample. In many embodiments, detecting is repeated, e.g., to detect a change in the viscosity of the fluid over two or more time points.

The methods can include blocking direct induction between the first and second inductors, but not blocking induction through the sample chamber, e.g., with an electromagnetic field shield.

In many embodiments of the methods, the first (field) inductor is inductively coupled to the second (sensor) inductor. In such cases, detecting an electrical parameter of the sample, can include detecting modulation of the current induced by the first inductor in the second inductor. That is, e.g., induction of current in the conductive sample fluid by the first inductor can result in a counter current in the fluid that generates a sample fluid field that modulates the effect of the first inductor field on the second inductor.

In certain preferred embodiments, accuracy and sensitivity of a sample analysis can be enhanced by comparing inductive effects on the test conductive fluid to inductive effects on a control fluid. In many embodiments, it is preferred to include at least high and low calibration reference standard samples in additional sample chambers to confirm the assay is reading accurately across the useful range.

DEFINITIONS

Unless otherwise defined herein or below in the remainder of the specification, all technical and scientific terms used herein have meanings commonly understood by those of ordinary skill in the art to which the present invention belongs.

Before describing the present invention in detail, it is to be understood that this invention is not limited to particular methods, devices or samples of interest, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a component" can include a combination of two or more components; reference to "sample" can include mixtures of samples, and the like.

Although many methods and materials similar, modified, or equivalent to those described herein can be used in the practice of the present invention without undue experimentation, the preferred materials and methods are described herein. In describing and claiming the present invention, the following terminology will be used in accordance with the definitions set out below.

An inductor is an electrical component that can store energy in a magnetic field created by the electric current passing through it. A "field inductor", in the context of the present methods and devices, is an inductor that is energized through electric contact with an electric voltage (e.g., from an electric oscillator) to generate an electromagnetic field. The resultant fields from field inductors are positioned and oriented to be inductively coupled to an electrically conductive sample when it is present in an associated sample chamber. The field inductor is structured to function in inducing a current in a sample present in the sample chamber. Typically an inductor is a conducting wire shaped as a coil, the loops helping to create a strong magnetic field, as outlined in Faraday's law of induction. A pair of structures (e.g., a sample in a chamber and/or inductors) are "inductively coupled" when they are arranged so that when an electric current is flowing in the first structure of the pair an electromagnetic field is generated that induces a counter-emf (voltage) in the second structure, as is known in the art.

A "sensor inductor", in the context of the present methods and devices, is an inductor that functions to provide a detectable output voltage (e.g., counter-emf) or current under the influence of an electromagnetic field, e.g., emanating from a conductive fluid in a sample chamber and/or from a field inductor. It is recognized that a field inductor can also act as a sensor inductor, e.g., responding to perturbations of a field generated by the same inductor. However, in most embodiments of the present methods and devices, there are separate sensor and field inductors, wherein the field inductor functions to transmit a field to a sample and/or sensor, and the sensor inductor functions to receive a field from a sample and/or field inductor and generate a detectable voltage.

"Viscosity" is a measure of the resistance of a fluid (including gels and semisolids) to deformation by either shear stress or extensional stress. In many conductive fluids, electrical currents are carried, at least in part, by ions in solution. In these cases, increased viscosity is often directly related to increased electrical resistance and/or impedance, e.g., due to increased resistance to carrier ion mobility.

A "field shield" is a structure that blocks penetration of electromagnetic lines of force. For example, a Faraday cage is an electromagnetic field shield. Depending on the frequency of the electromagnetic radiation, shield material can be a sheet or surface of conductive material. In some cases, the shield is a mesh of fabric of conductive material. Typically, the shield in electrically grounded.

A conductive sample in a sample chamber is "inductively coupled" to a field inductor when the inductor is arranged so that an electrical current flowing in the inductor will generate a field that induces an electric voltage or current in the sample. A conductive sample in a sample chamber is "inductively coupled" to a sensor inductor when the inductor is arranged so that an electrical current flowing in the sample will generate a field that induces a counter-emf in the inductor.

A "conductive fluid" is a fluid (including gels and semisolids) that is electrically conductive. It is recognized that conductivity is a matter of degree. However, conductive fluids of the present methods and devices are conductive enough, e.g., to have electric currents detectably (by sensors and detectors of the invention) induced by fields generated using field inductors of the invention. Typical conductive fluids of the invention have conductivities ranging from, e.g., at least about that of pure distilled water (about 0.04 µS/cm) to about the conductivity of a strong salt solution (e.g., about $10^6$ µS/cm), from about 0.1 µS/cm to about $10^5$ µS/cm, from about 1 µS/cm to about $10^4$ µS/cm, from about 10 µS/cm to about $10^3$ µS/cm, or about 100 µS/cm.

BRIEF DESCRIPTION OF THE DRAWINGS

FIG. 4A shows a top down view of an inner spiraling planar inductor coil with a first electrical lead in the same plane as the coil, and the second lead running in a different plane (e.g., different layer of a cartridge). FIG. 4B shows a side cross-sectional view of a sample chamber between a pair of inductors, wherein the electrical leads for the inductors are in different layers of a laminated structure.

DETAILED DESCRIPTION

The present inventions include devices and methods to evaluate, e.g., the conductivity or viscosity of a sample by detecting the sample's modulation of electromagnetic fields. In general, the devices of the invention include a sample chamber between a pair of inductors. Electric currents and fields induced in the sample by a field (transmitting) inductor can detectably affect electric currents induced in an associated sensor (receiving) inductor. The viscosity and/or conductivity of the sample can be determined, e.g., based on how the sample modulates the current induced in the sensor inductor.

The devices of the invention can include, e.g., a sample chamber between a sensor inductor and a field inductor. The field inductor can be energized with an oscillator circuit providing an AC current to conductors of the inductor. The sensor inductor can be monitored by a detection circuit that detects the status or changes in an electrical characteristic (e.g., voltage, current, resistance, or waveform) of the sensor inductor. The device can be packaged as a micro-machined cartridge, e.g., for reduced costs and reduced sample size.

The methods of the invention can include, e.g., flowing a sample into a sample chamber between two inductors. An alternating current (AC) is applied to one inductor to generate an electromagnetic field, inducing a counter current in the sample and/or in the second inductor. The counter current is detected by a detector. The absolute magnitude, change in magnitude, rate of change and/or waveform phase shift in an electrical parameter associated with the counter current can be correlated with, e.g., a conductivity or viscosity of the sample.

Figure 1:
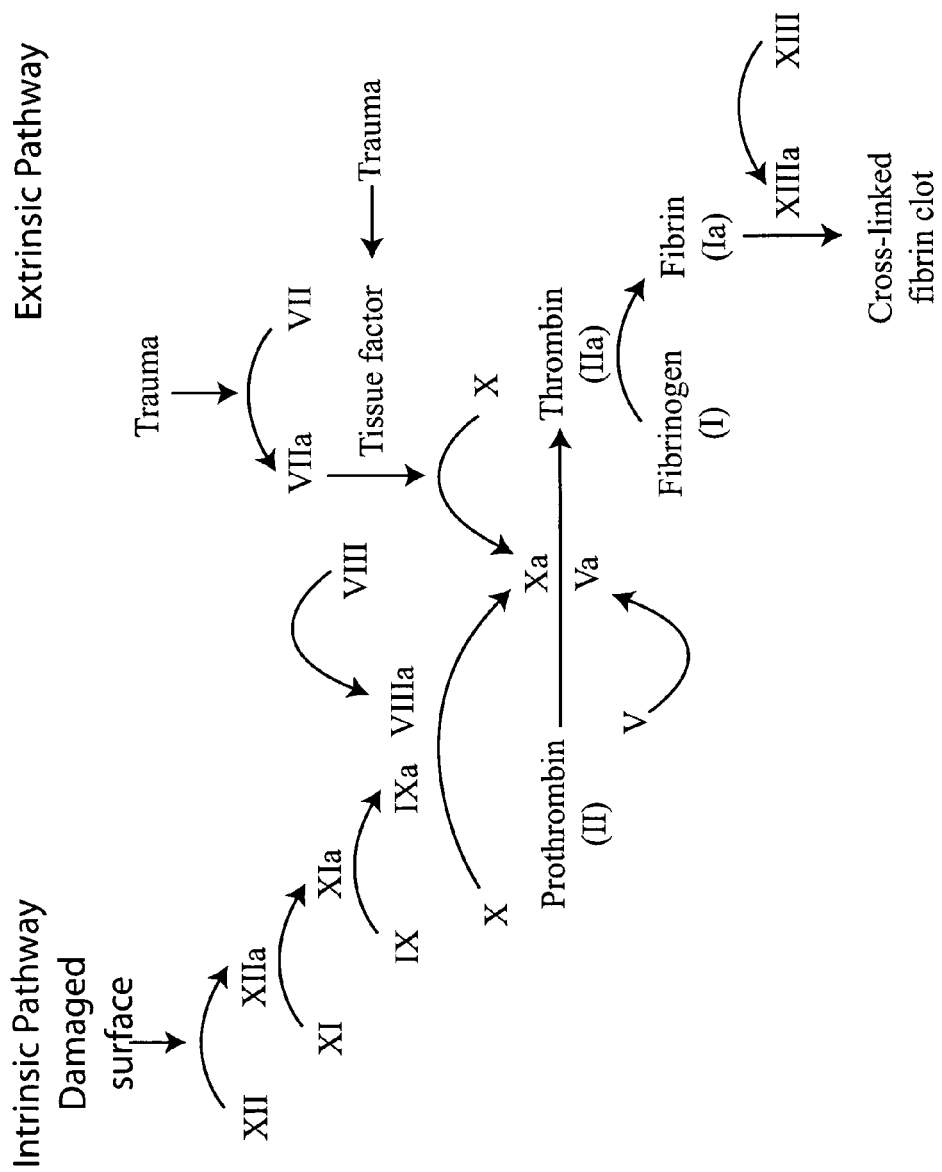
FIG. 1 is a flow diagram showing the classic blood coagulation cascade.

Many of the devices and methods of the invention can be used to evaluate coagulation in a blood sample. Blood coagulates according to a well established coagulation cascade of blood protein changes that lead ultimately to coagulation of the blood by conversion of fibrinogen to fibrin. Coagulation can be initiated along the intrinsic contact activation pathway or along the extrinsic tissue factor pathway, as shown in FIG. 1. The two initiation pathways converge at the common pathway wherein prothrombin is converted to thrombin. Thrombin is a serine protease that acts on soluble fibrinogen in plasma to convert it into elongate insoluble fibrin monomers that form a contracting gel (clot).

The intrinsic pathway is typically initiated by formation of the primary complex of high-molecular-weight kininogen (HMWK), prekallikrein, and factor XII on blood contact with exposed collagen. Prekallikrein is converted to kallikrein and factor XII becomes factor XIIa. Factor XIIa converts factor XI into factor XIa. Factor XIa activates factor IX, which forms a tenase complex with cofactor VIIIa, which in turn activates factor X to factor Xa. Activated factor Xa can initiate the final coagulation phase by converting prothrombin into thrombin, which coagulates fibrinogen. This pathway can be evaluated using the activated partial thromboplastin time (aPTT) assay.

The extrinsic tissue factor clotting pathway generates a "thrombin burst", to quickly stop blood flow in response to trauma. Following damage to a blood vessel, factor VII comes into contact with tissue factor (TF), which is present extravascularly in cells, such as stromal fibroblasts and leukocytes, to form an activated complex (TF-VIIa). In the brief following cascade, TF-VIIa activate factor X to factor Xa, which can convert prothrombin to thrombin. This pathway can be evaluated using the prothrombin time (PT) assay.

In the final common pathway, thrombin has a variety of functions. However, its primary role is the conversion of fibrinogen to fibrin, the building block of a hemostatic plug along with platelets. In addition, thrombin activates factors VIII and V and their inhibitor protein C (in the presence of thrombomodulin), and it activates Factor XIII, which forms covalent bonds that crosslink the fibrin polymers that form from activated monomers.

The function of the intrinsic pathway in a plasma sample can be determined using the activated partial thromboplastin time (aPTT) assay. Apart from detecting abnormalities in blood clotting, it is also used to monitor the treatment effects with heparin, a major anticoagulant. A phlebotomist collects blood samples in vacu-tubes with oxalate or citrate to arrest coagulation by binding calcium. The blood sample is then centrifuged to provide blood plasma. To activate the intrinsic pathway in an aPTT assay, phospholipid, an activator (such as silica, celite, kaolin, ellagic acid), and calcium (to reverse the anticoagulant effect of the oxalate) are mixed into the plasma sample. The activated partial thromboplastin time is essentially the time it then takes for a clot to form.

The aPTT can be used in conjunction with the prothrombin time (PT), which measures the function of the extrinsic pathway. In the PT assay, an excess of calcium is added (thereby reversing the anticoagulation effects of citrate) along with tissue factor (also known as factor III or thromboplastin). The PT result is essentially the time it takes tissue factor to coagulate a plasma sample at 37° C.

The present methods and devices can be used to evaluate the viscosity and/or conductivity of any number of fluid or gel samples. However, we note that the methods and devices are particularly well suited to the performance of blood coagulation assays, such as aPTTs and PTs. For example, plasma contains ionic salts that can conduct electric current. An electric current can be induced to flow in plasma by exposure to changing flux of an electromagnetic field. Further, the resistance of the plasma to the flow of an induced electric current can be affected by the coagulation state of the plasma. The electrical resistance of plasma, or changes in resistance with time, can be correlated to the coagulation status of the plasma, e.g., to determine a clot formation end point of a PT or aPTT assay.

Devices for Detection of Sample Conductivity

Figure 2:
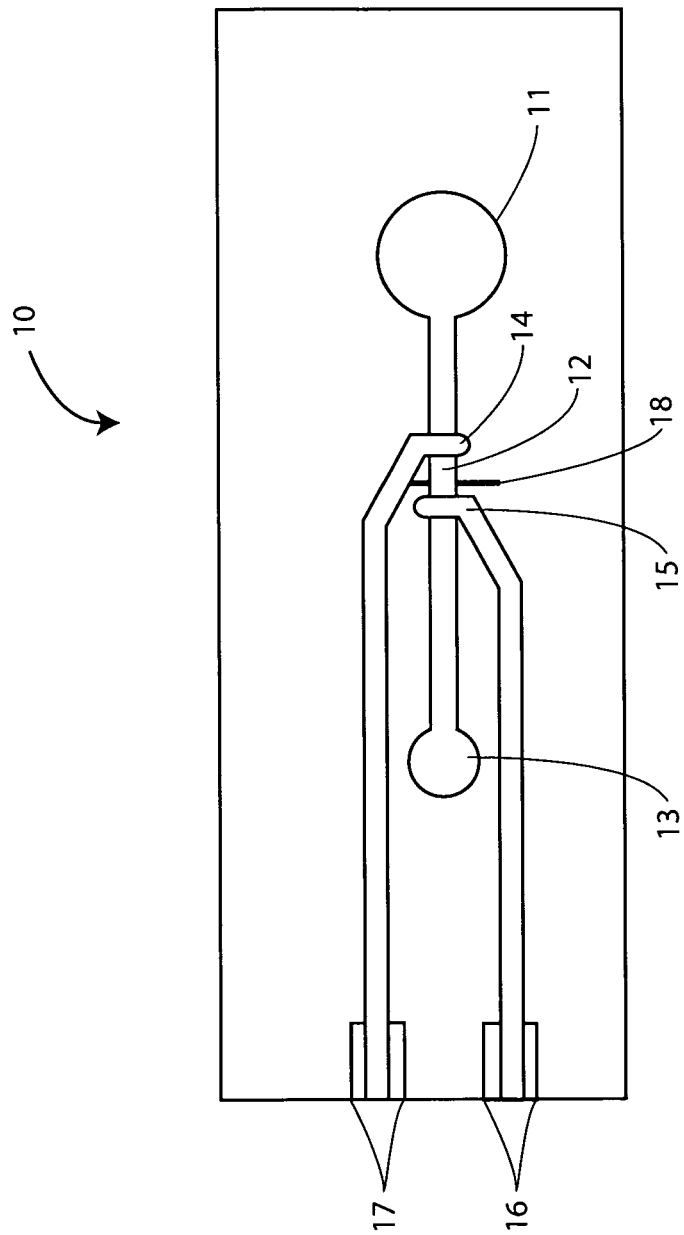
FIG. 2 is a schematic diagram of a fluid analysis cartridge wherein sample currents induced by a field inductor are detected by a sensor inductor.

Devices of the invention can include, e.g., a sample in a sample chamber between a pair of inductors. The first inductor can be in electrical contact with an oscillator circuit and the second inductor can be in electrical contact with a detector circuit. The device can be provided, e.g., in a micromachined cartridge, for lower cost, smaller sample size and consistent performance. For example, as shown in FIG. 2, the cartridge 10, can include a sample receiving port 11, in fluid contact with a sample chamber 12 and with a vented waste chamber 13. In one embodiment, a sensor inductor 14 can be positioned along the chamber at one position and a field inductor 15 can be positioned along the chamber at a second position. A pair of field electrodes 16 can be in electric contact with the field inductor (e.g., to provide voltages from an oscillator) and a pair of sensor electrodes 17 can be in electrical contact with the sensor inductor (to provide signals to a detector). Optionally, an electric field shield 18 can be positioned between the sensor inductor and field inductor, e.g., to reduce direct interaction between the inductors.

Typically, the cartridge of FIG. 2 would have a length of about 7 cm, width of about 2.5 cm and a thickness of about 4 mm. In most embodiments, the cartridge length ranges from about 15 cm to about 2 cm, or from about 10 cm to about 4 cm. The cartridge width typically ranges from about 4 cm to about 1 cm, or from about 3 cm to about 2 cm. The cartridge thickness ranges from about 10 mm to about 0.5 mm, or from about 5 mm to about 1.5 mm. Channels in the cartridges typically range in the milli-scale to the micro-scale. For example, the channels typically have at least one cross-sectional dimension ranging from about 2 mm to about 50 μm, or from about 1 mm to about 100 μm.

Figure 3:
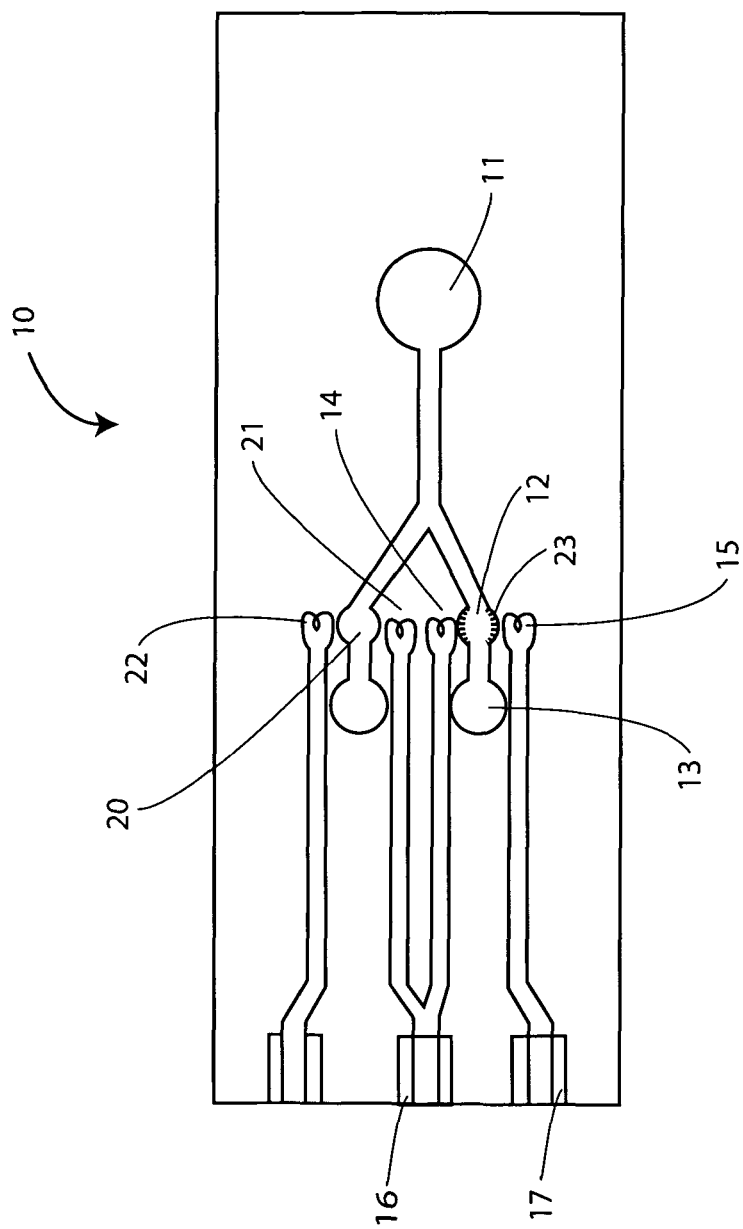
FIG. 3 is a schematic diagram of a cartridge for detecting induced electrical properties of a test sample in contact with a reagent. The cartridge provides for comparison of test sample responses to those of a negative control (without reagent or with a different reagent such as control reagent).

In many embodiments, the devices for detecting conductivity can include one or more additional (control and/or reference standard) chamber, e.g., between other pairs of inductors. In many cases, it is desirable to include at least two additional sample chambers to run a pair of standards having high and low levels of reagents or analytes of interest. For example, as shown in FIG. 3, a control or reference chamber 20 can be provided between a second (control) field inductor 21 and a second sensor inductor 22. In certain embodiments, an activation reagent 23 can be provided in the first chamber 12, e.g., to initiate a sample reaction, such as plasma clotting.

Inductors

Field inductors in the devices receive a changing electric current to generate a primary electromagnetic field. The field can interact with electrically conductive materials in a sample chamber, resulting in, e.g., a current in the sample and associated counter field from the sample, and/or detectable modulations in the primary field. Sensor inductors in the devices receive electric fields, e.g., emanating from the field inductor and/or sample chamber, resulting in induced currents in the sensor inductor that can be detected by an appropriate detector.

Field and sensor inductors in the devices can be configured in any suitable way to functionally interact with the other associated components in the device. For example, the inductors can have a size, shape, orientation and materials appropriate for a particular embodiment. The inductors can be in circuits with power sources or detectors. The inductors are configured and oriented for functional inductive coupling to samples in the sample chamber.

The inductors can range in size, e.g., from macro-scales for industrial processing and analysis applications to micro-scales for microfluidic assay applications. For example, the inductors can have at least one dimension (or all dimensions) ranging in size from about 10 cm or more to about 10 μm or less, from 1 cm to 100 μM, or about 1 mm.

The inductors can have any suitable shape. For example, the inductor can have, e.g., a straight conductive path. However, linier inductors typically do not provide optimum field transmission or field reception in many embodiments. In preferred embodiments, the sensor inductor and/or field inductor are fabricated to include a flat or helical coil arrangement.

Figure 4A:
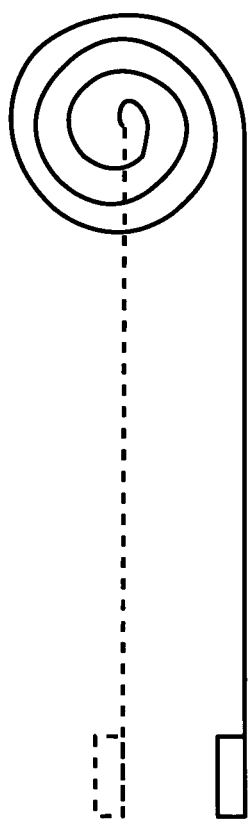
FIGS. 4A and 4B are schematic diagrams of devices having inductors with a planar aspect ratio.
Figure 4B:
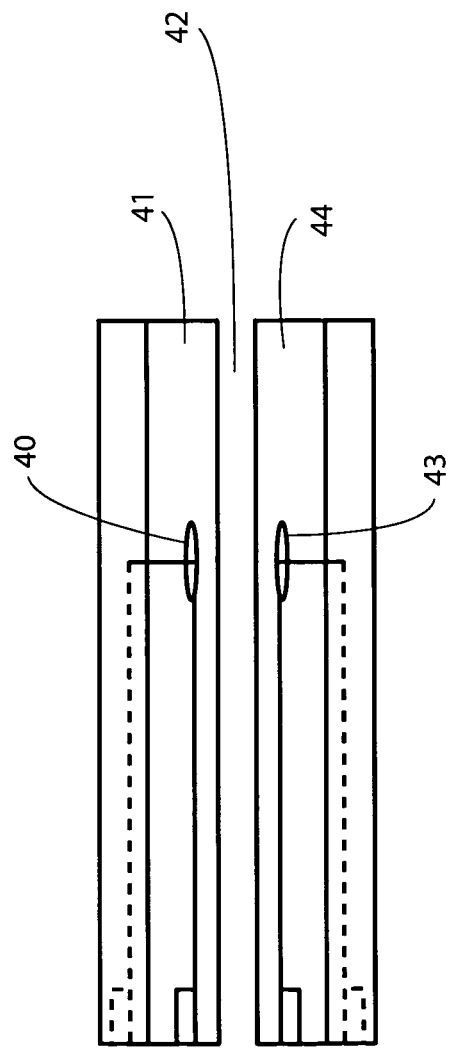

As shown in FIG. 4A, the inductor can be configured as a flat coil with the conductor spiraling out in a plane from a central electrode to an outer electrode. The flat inductor can have any desirable configuration, e.g., in a cartridge having multiple laminated layers. As shown in FIG. 4B, a first coil 40 can be in a layer 41 above the sample chamber 42; and a second coil 43 can be in a different layer 44 below the sample chamber. The coil can be manufactured, e.g., by lithography, as a flat coil in one layer, e.g., with a first electrode and lead in the same layer as the coil and with the second electrode and lead contacting the other end (typically the inner end) of the coil conductor from another insulated layer.

Figure 5:
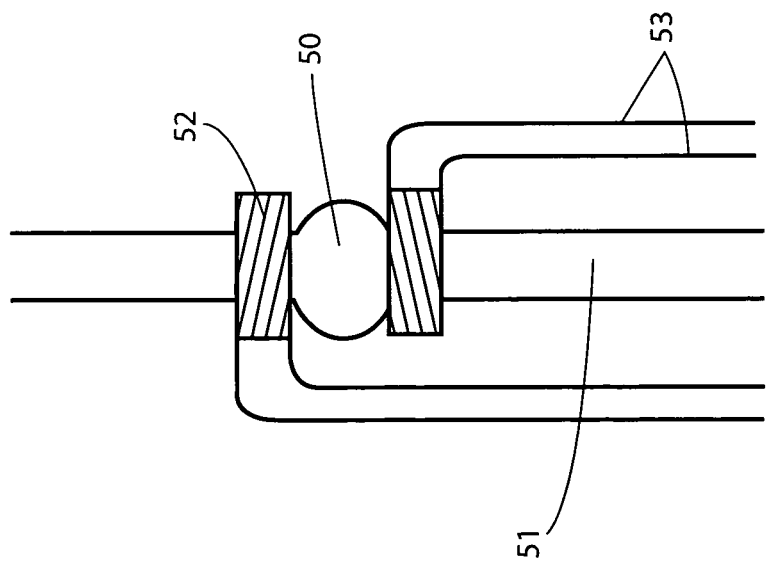
FIG. 5 shows a schematic diagram of a tubular sample chamber between inductors positioned around inlet and outlet ports of the chamber.

In other embodiments, the inductor conductor can spiral progressively about an axis (e.g., in a helix). For example, the inductor can be a wire conductor wound about a central core, as shown in FIG. 5. The sample chamber 50 can be, e.g., a cylindrical conduit or expanded chamber in a conduit 51. One or both the inductors 52 can be wires wound around the chamber central axis, with leads 53 to, e.g., an oscillator or detector.

Inductors can be made of any suitable conductive material. For example, the inductor can be fabricated from a semiconductor, copper, silver, and the like. Optionally, the inductors can be on a flexible circuit on substrates such as polyimide, Kapton™, liquid crystal polymer, PET and/or the like.

The inductors can have a core. The core can be, e.g., the sample chamber (typically enclosing a conductive fluid sample) or a conduit in fluid contact with the sample chamber. Optionally, the core can include a ferromagnetic material, such as iron, to strengthen or focus the electromagnetic field.

Many embodiments of the devices include paired field and sensor inductors. For example, a first (field) inductor is in electrical contact with an oscillator circuit, thereby generating an electromagnetic field that contacts the sample chamber, and optionally contacts a sensor inductor. Depending on how a sample in the sample chamber modulates the field, currents induced in the sensor inductor will also be modulated. Characteristics of the sample can be correlated to aspects of the current induced in the sensor inductor.

Optionally, devices of the invention can have a single inductor associated with the sample chamber. For example, a field generating inductor can expose a sample in the chamber to an electromagnetic field. Electrodes of a detector can be in direct contact with the sample to detect induced phenomenon, such as a voltage, current, resistance or waveform, in the sample. Alternately, electrical phenomenon induced in the sample by the inductor field can be detected by the field inductor itself (e.g., also acting as a sensor inductor). For example, when the filed inductor induces a current in the sample, the current in the sample will produce a counter field and detectable counter-emf back in the field inductor. The counter-emf can be correlated to characteristics of the sample. For example, the difference between the field inductor current or voltage when there is no sample in the chamber and when there is a sample, can be correlated to the conductivity or viscosity of the sample. Optionally, changes in a sample with time can be detected by changes in the field inductor voltage or current. In one aspect, a comparator can compare the output of the oscillator powering the field inductor and the current actually present in the field coil. Optionally the comparison can be against a control sample, e.g., in a control sample chamber.

The field inductor is preferably oriented so that the electromagnetic field generated is functionally directed to the sample chamber and/or to a sensor inductor. The sensor inductor is preferably oriented so to functionally receive fields generated and/or modulated by a sample in the sample chamber.

Oscillators

To induce a current in a sample held in the sample chambers of the invention, the field inductor must generate a changing electromagnetic field. Switching on a DC current can provide a field that expands to possibly generate a current spike in the sample. A square wave of pulsating DC can result in repeated creation and collapse of a field, to produce a series of current spikes in the sample. However, it is preferred to provide an AC current to the field inductor, e.g., for a continuously changing field that continuously induces changing currents in the sample.

An oscillator can provide energizing AC current to the field inductor. The oscillator can be any suitable, e.g., to provide the field requirements of the device and a proper impedance match to the inductor. In preferred embodiments, the oscillator has an output frequency ranging from more than about 10 MHz to less than about 100 Hz, from about 500 kHz to about 1 kHz, from 200 kHz to about 10 kHz, from 100 kHz to about 50 kHz. In some embodiments, the oscillator is tuned to provide a frequency of about 25 kHz while driving the field inductor.

Oscillators can be integral with the device component comprising the sample chamber and field inductor, or can be a separate piece of device hardware. In a preferred embodiment, the sample chamber is in a disposable cartridge separate from the oscillator and/or field inductor.

Detectors

Detectors can be functionally coupled to sensors of the devices, e.g., to detect the magnitude and/or quality of an electrical parameter in a sample of interest in the sample chamber. For example, the detector can be in electrical contact with a sensor to detect an electrical property of a sample.

In many embodiments of the devices, the detectors detect an electrical parameter resulting from inductive contact of the sample with the field inductor. For example, the detector can be in electrical contact with sensor electrodes in electrical contact with the sample to detect, e.g., a voltage, current, resistance, wavelength, phase shift, and/or the like, induced into the sample by an electromagnetic field emanating from the field inductor. In other embodiments, the detector interacts with a sensor inductor to detect an electromagnetic field emanating from the sample, from the field inductor, and/or to detect modulatory effects of the sample (e.g., counter-emf) on the field inductor field. The detections provided by the sensor inductor can directly or indirectly reflect electrical phenomenon in the sample, such as, e.g., voltages, currents, resistance, wavelengths, phase shifts, and/or the like, in the sample. We note that measurement of one electrical parameter can indirectly measure another. For example, because current is directly proportional to voltage and inversely proportional to resistance, given one or two parameters inferences can be made as to other parameters.

In a certain embodiment, the field inductor also acts as the sensor inductor, as discussed above. For example, while the oscillator circuit energizes the inductor with a certain waveform (amplitude and frequency), the presence of the sample can detectably change the waveform ultimately present in the inductor windings or field. The change can be detected by a detector in electrical contact with the inductor circuit. The changes in the inductor over the oscillator input waveform can be correlated with characteristics (impedance, resistance, current, viscosity, and the like) of the sample.

Sample Chambers

Sample chambers of the devices provide, e.g., a space to hold a sample in close proximity to a field inductor so that the sample can be inductively coupled functionally to the inductor. Typically, the sample chamber is also in functional contact with a detector sensor means.

In many cases, the sample chamber is a section of a conduit in functional proximity to the field inductor. Often, the sample chamber is a section of the conduit with an expanded cross section, e.g., to provide a greater sample exposure to the inductor field, and/or to screen out a substantial portion of direct interaction between the field inductor and sensor inductor. Provision of inlet and outlet conduits, to and from the sample chamber can facilitate introduction of a sample, or repeated changes of samples, into the chamber. Alternately, the sample chamber can simply have an inlet port where sample is introduced directly, e.g., with a pipettor.

It is preferred the chamber be fabricated from a material that is not electrically conductive, so that the chamber itself will not block interaction between the sample and inductors of the devices. Preferred materials for sample chambers are glasses and plastics.

In many embodiments, it is desirable to provide temperature control to the sample chamber. For example, the sample chamber can be adjacent to a large heat sink that stabilizes the temperature of the chamber and sample. Optionally, the sample chamber can have an associated thermostat circuit to control the temperature. For blood coagulation assays, the sample chamber should typically be held at about 37° C.

Sample chambers can vary in size, e.g., depending on the size of available samples and the desired configuration and scale of intended inductors. Sample chambers of the devices can range in volume from more than about 10 ml to less than about 1 µl, from about 1 ml to about 2 µl, from about 200 µl to about 3 µl, or from about 50 µl to about 4 µl or about 5 µl. The sample chambers can be macro-scale, e.g., with at least one dimension greater than about 1 cm. Preferably, the sample chambers are micro-scale, e.g., with at least one dimension less than about 5 mm, less than 1000 µm, less than 100 µm, or less. In many cases the sample chambers are of a size that provides fluid flow and filling by capillarity.

Sample chambers can have at least one inner wall surface in close proximity to at least one inductor; typically, a field inductor. The inductor can be more than 10 mm from the nearest sample chamber inner wall surface, but typically less than 10 mm, less than 5 mm, less than 1 mm, 0.1 mm or less. In certain embodiments, the inductor can be in contact or provide an inner surface of the sample chamber.

In many embodiments of the devices, the sample chamber is defined as a void in a laminated layered structure. For example, a first layer of material can have a cut out section in the desired shape of the sample chamber. The first layer can include cut outs (e.g., defining side walls) for additional spaces, such as, e.g., channels, reaction chambers, waste chambers, and the like. The first layer can be laminated between a top cover layer and a bottom substrate layer, thereby functionally sealing the voids designed into the first layer. In preferred embodiments, the sample chamber fills an area between the field inductor and sensor inductor, e.g., so that there is no direct line between the inductors that does not go through the sample chamber. The top and bottom layers can comprise inductors and/or sensors adjacent to the sample chamber space. Alternately, inductors can be built into the same layer as the sample chamber void.

Optionally, the sample chambers can be, e.g., tubular conduit with the inductors running along or wrapped around the axis of the conduit, e.g., as shown in FIG. 5. In a preferred embodiment, the sample chamber has an increased cross section in a space between the field inductor and sensor inductor. In a more preferred embodiment, the sample chamber cross section has size and dimensions large enough to include all direct lines between the field and sensor inductors. In still other embodiments, the cross section is large enough to cross most of the electromagnetic lines directed toward the sensor inductor from the field inductor.

The sample chamber can comprise one or more reagents. The reagents can react with one or more sample constituents (e.g., analytes of interest) to provide a detectable product. For example, the sample chamber can include reagents used to activate the intrinsic and/or extrinsic coagulation cascade, e.g., according to protocols for PT or aPTT coagulation assays. Optionally, the reagents can be present in a conduit or reaction chamber leading into the sample chamber, e.g., so that the sample can begin reacting before it flows into the sample chamber for detection.

The devices of the invention can include multiple sample chambers, e.g., to provide comparison controls and/or confirmatory assays. For example, a cartridge of the inventive devices can include conduits through which fluids can separately flow to a negative control sample chamber without reagents and to a test sample chamber with reagents, e.g., as shown in FIG. 3. Such an arrangement can substantially enhance the precision and sensitivity of an assay by allowing subtraction of non-specific background and electrical interference from the test detections. Optionally, the cartridge can include multiple test sample chambers for replicate testing of the same sample, or testing of multiple different samples on the same cartridge at once.

Samples introduced into the sample chambers can include any electrically conductive fluid of interest. For example, the sample can be an aqueous solution, a biological fluid, a control solution, whole blood, anti-coagulated plasma, plasma, synovial fluid, CSF, amniotic fluid, and the like.

Electric Field Shields

In certain embodiments of the devices, electrical characteristics of the sample can be more precisely and sensitively determined if the sensor inductor is shielded to some extent from the field inductor with a field shield. Preferably, the shielding is configured to minimize shielding of the sample from the field inductor. In this way, a greater portion of fields detected by the sensor emanate from, or are modulated by, the sample.

Field shields can be said to "block" field lines. One way to demonstrate such blockage is to show the change in field lines before and after installation of the shield. For example, one can identify the field lines, e.g., between a field inductor and sensor inductor, then a shield can be mounted between the inductors. Lines that were present before mounting the shield but absent after mounting the shield have been blocked. In many cases, it is desirable to block lines "directly" between the inductors, and/or those lines that diverge outwardly in a loop while progressing between the pair of field and sensor inductors. In many cases, it is desirable to not block field lines that are directed to or through the sample chamber or sample fluid.

In one aspect of the invention, the field inductor is essentially enclosed in a Faraday cage but having a port allowing illumination for the sample chamber by the field, while not allowing undue stray field lines to reach the sensor inductor without first traversing the sample chamber.

An electric field shield can be, e.g., a grounded conductive wall, layer, fabric or mesh, e.g., that blocks field lines from reaching the sensor without interacting with a sample in the sample chamber. In one aspect, the shield can be a partition extending out from the sample chamber and across the space between the field and sensor inductors. In other aspects, the shield can be a cage blocking extraneous fields emanating from the ambient environment of the device from reaching any of the sample, field inductor or sensor inductor; thereby reducing background noise in the system.

Methods of Detecting Conductivity Changes

Conductivity of a sample in a sample chamber can be detected by inducing a current in the sample with an electromagnetic field from an inductor, and detecting a current induced in the sample by the field. Electrical characteristics of a sample can be related to the viscosity of the sample. In a typical embodiment of the present methods, the viscosity of a sample is monitored over time by placing the sample in a chamber with a reagent that initiates gelation, exposing the sample to an electromagnetic field, monitoring a counter-emf (or associated field) from the sample, and correlating the counter-emf to the viscosity of the sample. Typically, the counter-emf is monitored with a sensor inductor that directly detects a field emanating from the sample, and/or by detecting perturbations in the initial field inductor field caused by the counter-emf of the sample.

Providing Samples

Samples for analysis by the methods can be any amenable to the detection techniques. Typically, the samples are electrically conductive fluids, gels or semisolids. The methods are particularly well suited to detecting conductivity in aqueous solutions of ionic compounds. Because migration of ionic carriers can be impeded by the viscosity of a solution, the methods are well suited to detecting viscosities or changes in viscosities of a sample.

Samples for analysis according to the methods can be organic, inorganic or aqueous fluids, solutions, gels semisolids or solids that can be induced with an electromagnetic field to generate an electric current or voltage. It is envisioned that the present methods and devices can be used to monitor polymerization of conductive plastics compositions. Preferred samples include aqueous salt solutions, salt solutions comprising one or more denaturable peptides or organic polymers, biological fluids, and the like. More preferred samples include, e.g., whole blood, plasma, serum, cerebrospinal fluid (CSF), amniotic fluid, synovial fluid, aqueous humour, exudates, and the like. In many cases, the samples are treated to prevent coagulation, then activated to initiate coagulation, before or during testing. In many cases, the sample is centrifuged or filtered before testing.

A common sample for testing is a blood sample. Whole blood is typically obtained by venipuncture into a tube containing a suitable anticoagulant. Whole blood can also be obtained from finger punch and can be used directly in assays. The blood cells and platelets are removed from the whole blood to provide blood plasma. Optionally, test cartridges of the invention can include a porous filter bed, e.g., in a sample port or a flow channel to remove blood cells as plasma flows into the sample chamber, e.g., by capillary action.

Samples can be introduced directly or manually into the sample chambers, or the sample of interest can flow to the sample chamber through a conduit, e.g., from another chamber. In many cases, the sample is introduced into a sample receiving port to flow to the sample chamber under the force of gravity, capillary action, or a pressure differential. In many cases, the sample fluid is filtered and comes into contact with a reagent as it flows to the sample chamber. In methods designed to provide a PT and/or aPTT assay to plasma, the sample is contacted with reagents to neutralize any anticoagulant and to initiate the intrinsic or extrinsic clotting pathway.

In certain embodiments, a negative control sample is also provided for comparison to a test sample in the methods. For example, the sample of interest can be analyzed in series or parallel, with or without reagents, e.g., so that extraneous influences on the analysis can be subtracted out. For example, readings of a sample in the sample chamber can be taken, reagents can be added to the sample and the readings taken again for comparison. Optionally, the cartridges of the invention can include a pair of identical sample chambers, exposed to the same electromagnetic field, but sample in only one chamber is treated with active reagents. In this way, treated and untreated samples can be read in parallel, and variances due to field instability can be negated. Optionally, the cartridges of the invention can include additional channels and sample chambers for parallel determinations of, e.g., positive controls, negative controls, and/or a range of standard reference analytes or reagents.

Providing Device Structures

Devices to practice the methods of the invention can be provided, e.g., as described above, in the Devices for Detection of Sample Conductivity section. Briefly, a sample chamber is provided in functional proximity to a field inductor for inductive coupling to a sample in the chamber. A sensor, such as paired sensor electrodes or a sensor inductor are provided to detect changes in electrical characteristics that may be induced in a sample by the field.

An oscillator can be provided to energize the field inductor. The oscillator can be tunable, so a desired waveform frequency and/or amplitude can be selected.

A comparator can be in contact with the oscillator circuit, and with the sensor circuit, to resolve differences between the oscillator or field signal and the signal picked up by the sensor. In this way, the influence of the sample on, e.g., field strength, field wavelength, waveform shape, waveform phase shift, and the like, can be determined.

A sensor can be provided to detect phenomenon resulting from interaction of the sample with the field from the field inductor. Detecting can be sensing a voltage, current, wavelength, wave phase shift, resistance, impedance, reluctance, and/or the like associated with currents or voltages induced in the sample. The sensor can be associated with amplification circuits to strengthen the detected signal. The sensing can be associated with band pass filters to reduce non-specific background.

The devices can include incorporated or free standing logic circuits and data storage devices (e.g., computers), for analysis and storage of assay results. For example, analog signals received can be converted to digital signals, e.g., using an A/D converter. The digital information can be analyzed according to established algorithms and correlations, e.g., to provide an assay output in a standardized form.

Sensing can include monitoring a sensor signal over time. Changes in sensor signals can be correlated to a condition of the sample, such as, e.g., a clotting time end point.

Correlating Signals to a Sample Characteristic

Signals from sensors can be correlated to a characteristic of the sample. Single time point measurements of a sample voltage, current, resistance or waveform can be correlated to, e.g., an ionic strength, temperature, extent of polymerization and/or viscosity of a sample at that point in time. Optionally, a time point of interest in a changing sample can be determined based on a signal reaching a certain magnitude, or rate of change end point.

To determine the condition of a sample at a given time, a detected signal can be correlated to a standard curve. For example, a regression curve can be developed presenting a range of conductivities for standard samples versus their associated coagulation state. The coagulation state of an unknown test sample can then be determined from the chart by reading the state correlated to a conductivity determined for the test sample.

In an embodiment of the invention, activated partial thromboplastin times for a variety of different standard samples can be determined according to standard methods. The standard samples can then be analyzed using a device of the invention to determine, e.g., a conductivity, or rate of conductivity change, for each sample, e.g., which correlates with the known aPTT times for the samples. From this data, a standard regression curve can be constructed correlating known aPTT times to conductivity values, or rate of conductivity change values, for the samples. Given the standard regression curve, the aPTT time for an unknown sample can be determined based on a conductivity, or rate of conductivity change, determined according to the methods of the invention.

EXAMPLE

Prothrombin Time (PT) in a Micro-Scale Device

The following examples are offered to illustrate, but not to limit the claimed invention.

The prothrombin time (PT) measures the function of the coagulation extrinsic pathway. In a clinical setting, the PT is used to determine the clotting tendency of blood, monitor warfarin dosage, to detect liver disease, and can suggest a vitamin K deficiency. The normal range for prothrombin time is usually around 12-15 seconds.

In a standard PT assay time, blood is drawn into a test tube containing liquid citrate, which acts as an anticoagulant by binding the calcium in a sample. The blood is mixed, then centrifuged to separate blood cells from plasma. An excess of calcium is added (thereby reversing the effects of citrate), along with tissue factor (also known as factor III or thromboplastin). The time the sample takes to clot at 37° C. is traditionally detected mechanically or optically.

A PT can be determined using the methods and devices of the present invention. For example, in view of FIG. 3, citrate anti-coagulated blood plasma is introduced into sample receiving port 11, which has a porous matrix filter effectively trapping particles larger than about 50 μm. The plasma flows through channels by capillary action to fill the test and control sample chambers, 12 and 20. Excess plasma flows into vented waste chambers 13. In the test side channel or in the test sample chamber, the plasma comes into contact, and mixes with reagents 23 comprising calcium salts and thromboplastin, thus initiating coagulation of the test sample.

An oscillator in electrical contact with field electrodes 16 provides an AC current of 200 MHz to field inductors 14 and 21. The oscillating electric current in the field inductor circuit generates an electromagnetic field that is coupled to the conductive blood plasma samples in the sample chambers, thus inducing an alternating current in the plasma.

Electric currents are also induced in sensor inductors 15 and 22 by the field inductors. However, the counter-emf currents in the control and test samples generates fields that modulate the shape, phase and amplitude of the currents induced in the sensor inductors. Detector circuits in electrical contact with sensor electrodes 17 of the test and control sensor inductors detect the currents induced in the sensor inductors.

A logic circuit, e.g., with a comparator function, in the detector compares the currents induced in the test and control sensor circuits. At early time points, the plasma sample is uncoagulated in both the test and control sample chambers. However, as coagulation progresses in the test chamber, resistance to electrical current flow (e.g., impedance) in the test sample increases, resulting in progressively less modulation (e.g., to phase shift angle θ and amplitude) of the inductor field received at the test sensor inductor with time.

A computer receives and stores the comparator data over a series of time points. The difference is field modulation between the test and control samples varies in a sigmoid fashion with time. For example, there is no significant difference between the test and control at the start of the assay, but this is followed by increasingly rapid differences. At a certain point, the rate of change (charted slope) in the modulation difference reaches a maximum. The difference then changes more slowly and levels off to approach a plateau. Any point in the sigmoid curve can be selected as an end point in the assay and correlated to standard PT assays, e.g., on the same samples. However, the most precise and repeatable end points for use in the assay are typically the inflection point of maximum slope (highest rate of change) and the time point where the difference is half way between the starting difference and plateau difference. These end points are readily determined by commonly available data analysis software.

The selected end time points can be reported out directly as clotting times determined by the device. Optionally, the time points can be correlated to standard PT times, e.g., using a regression curve, and reported out as standard PT results.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, many of the techniques and apparatus described above can be used in various combinations and permutations, all of which cannot reasonably be recited individually in this document, but can be understood by one of skill in the art on review of this specification.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A device to measure viscosity changes of a sample, the device comprising:

a sample port fluidly coupled to a sample chamber;
a sample with changing viscosity in the sample chamber;
a field inductor inductively coupled to the sample;
a sensor inductor inductively coupled to the sample; and,
an electronic detector in electrical contact with the sensor inductor;
whereby induction of a voltage or current in the sensor inductor by the field inductor detectably varies as the sample viscosity changes, thereby measuring viscosity changes in the sample.

2. The device of claim 1, wherein the device is a microfluidic device.

3. The device of claim 1, wherein the sample is stationary in the sample chamber during the viscosity changes.

4. The device of claim 1, wherein the sample is in contact with a reagent that changes the viscosity of the sample.

5. The device of claim 1, wherein the detector measures a voltage, a current, a resistance or a phase shift in the sensor inductor.

6. A viscosity sensor comprising:
a field inductor;
a sensor inductor, separate from the field inductor; and,
a sample chamber comprising an electrically conductive sample of changing viscosity,
wherein the sample is inductively coupled to the field inductor and inductively coupled to the sensor inductor.

7. The sensor of claim 6, wherein the sample chamber is in a laminar cartridge and positioned in a sample layer having opposite parallel planar surfaces, and
wherein the field and sensor inductors are positioned on opposite sides of the sample layer.

8. The sensor of claim 6, wherein the sample chamber is tubular with a central axis, and wherein the field inductor or sensor inductor is a conductor coiled around the axis.

9. The sensor of claim 6, wherein the sample is selected from the group consisting of: a polymerizing plastic, blood, synovial fluid, placental fluid, CSF and plasma.

10. The sensor of claim 6, further comprising an electric field shield between the field inductor and sensor inductor.

11. The sensor of claim 6, further comprising a reagent in the sample chamber active in polymerizing or coagulating the conductive fluid.

12. A sensor in a layered microfluidic cartridge, wherein the sensor comprises:
a field inductor in a first layer of the microfluidic cartridge;
a sample chamber in a second layer of the cartridge between the first layer and a third layer; and
a sensor inductor in the third layer of the cartridge;
wherein a conductive fluid in the sample chamber would be inductively coupled to the field inductor and to the sensor inductor.

13. The sensor of claim 12, wherein the field inductor or sensor inductor comprises a conductive material coiled within a plane substantially parallel to the second layer.

14. The sensor of claim 12, further comprising an electric field shield between the first and second inductors.

15. The sensor of claim 12, further comprising the conductive fluid in the sample chamber.

16. A sensor comprising:
a sample conduit having a central axis;
a field inductor of conductive material coiled around the sample conduit at a first position;
a sensor inductor of conductive material coiled around the sample conduit at a second position separated from the first position by a sample space distance along the axis;
a sample chamber in the conduit in the region of the sample space separation; and,
an electric field shield between the inductors, wherein the shield blocks electromagnetic field lines running between the field inductor and sensor inductor;
whereby a conductive fluid in the sample space would be inductively coupled to the field inductor and inductively coupled to the sensor inductor.

17. The sensor of claim 16, wherein the shield blocks electromagnetic field lines that run between the sensor inductor and field inductor without passing through the sample chamber sample space.

18. The sensor of claim 16, further comprising a detector in electrical contact with the field inductor or sensor inductor, which detector measures a parameter selected from the group consisting of: a voltage, a current, a waveform or a phase shift.

19. The sensor of claim 16, further comprising the conductive fluid in the sample chamber.

20. A sensor comprising:
a field inductor inductively coupled to a sample chamber comprising an inner surface;
one or more detector electrodes in electrical contact with the inner surface; and,
an electronic detector in electrical contact with the sample chamber surface through the detector electrodes;
whereby an electrical current induced by the inductor on a sample in the sample chamber is detected to determine an a viscosity, a voltage, a current, a waveform or a phase shift in the sample.

21. A method of determining a viscosity of a conductive fluid, wherein the method comprises:
providing a sample chamber inductively coupled to a field inductor and to a sensor inductor;
providing a conductive fluid in the sample chamber;
providing an electronic detector in functional contact with the sensor inductor;
generating an electric field with the field inductor;
detecting with the detector an electric current or voltage induced in the sensor inductor by the electric field; and,
evaluating the detected current or voltage to determine the viscosity of the sample.

22. The method of claim 21, wherein the conductive fluid is selected from the group consisting of: whole blood, polymerizing plastic, synovial fluid, CSF, placental fluid and blood plasma.

23. The method of claim 21, wherein the electric current or voltage is induced or modulated by an electric field generated by a current flowing in the conductive fluid.

24. The method of claim 21, further comprising blocking electromagnetic lines of force between the first and second inductors, but not blocking lines through the sample chamber.

25. The method of claim 21, further comprising detecting a change in the viscosity of the fluid with time by detecting the current or voltage at two or more time points.

26. The method of claim 25, wherein the change in viscosity with time is detected while the fluid is not flowing.

27. The method of claim 21, wherein the field inductor is inductively coupled to the sensor inductor, and wherein said detecting comprises detecting modulation of a current induced by the field inductor in the sensor inductor, wherein said modulation results from induction of the sensor inductor by a current in the conductive fluid.

28. The method of claim 21, further comprising comparing the viscosity of the conductive fluid to a viscosity of a control fluid or to a reference standard.

29. The method of claim 21, wherein said evaluating comprises determining a phase shift between the field inductor and sensor inductor, or between the field inductor and the conductive fluid.

30. The method of claim 21, further comprising contacting the conductive fluid with a reagent that influences the viscosity or conductivity of the conductive fluid.

\* \* \* \* \*